United States Patent [19]
Getty et al.

[11] Patent Number: 6,031,565
[45] Date of Patent: Feb. 29, 2000

[54] STEREO RADIOGRAPHY

[75] Inventors: David James Getty, Bedford; Allan William Frederick Huggins, Arlington, both of Mass.

[73] Assignee: GTE Internetworking Incorporated, Burlington, Mass.

[21] Appl. No.: 09/160,299

[22] Filed: Sep. 25, 1998

Related U.S. Application Data

[63] Continuation of application No. 08/079,363, Jun. 18, 1993, abandoned.

[51] Int. Cl.[7] ........................................... H04N 5/32
[52] U.S. Cl. ..................................... 348/56; 348/51
[58] Field of Search .................... 348/42, 47, 51, 348/56, 77; 250/370.08, 370.09; 378/46, 87, 90, 98.2, 98.4, 98.6; 382/128, 132; 604/20; H04N 5/32

[56] References Cited

U.S. PATENT DOCUMENTS

| | | | |
|---|---|---|---|
| 3,076,054 | 1/1963 | Simon | 178/6.5 |
| 3,309,519 | 3/1967 | Euler et al. | 250/60 |
| 4,212,072 | 7/1980 | Huelsman et al. | 348/163 |
| 4,578,802 | 3/1986 | Itoh | 378/41 |
| 4,596,028 | 6/1986 | Gabbay | 378/41 |
| 4,627,087 | 12/1986 | Marks | 378/4 |
| 4,658,410 | 4/1987 | Haendle et al. | 378/41 |
| 4,727,565 | 2/1988 | Ericson | 378/205 |
| 4,769,701 | 9/1988 | Sklebitz et al. | 358/111 |
| 4,875,478 | 10/1989 | Chen | 128/303 |
| 5,003,571 | 3/1991 | Kido | 378/99 |
| 5,018,176 | 5/1991 | Romeas et al. | 378/37 |
| 5,090,038 | 2/1992 | Asahina | 378/41 |
| 5,142,642 | 8/1992 | Sudo | 348/56 |
| 5,175,616 | 12/1992 | Milgram et al. | 348/47 |

OTHER PUBLICATIONS

Gonzalez et al, Digital Image Processsing, Image Enhancement, pp. 166–170, 1992.

*Primary Examiner*—Richard Lee
*Attorney, Agent, or Firm*—Leonard Charles Suchyta; Floyd E. Anderson

[57] ABSTRACT

In the stereo radiographic system, an electronic x-ray image detector is exposed, through a three dimensional object to be viewed, with x-rays successively from two points separated by a preselected angle. The respective signals generated by the x-ray image detector during the successive exposures are digitized and stored. A video display is driven to generate, on successive frames, alternating images based on respective ones of the stored signals and the eyes of a user viewing the display are alternately occluded in synchronism with the alternation of the images thereby to provide to the user a stereoscopic densitometric view of the three dimensional object.

9 Claims, 9 Drawing Sheets

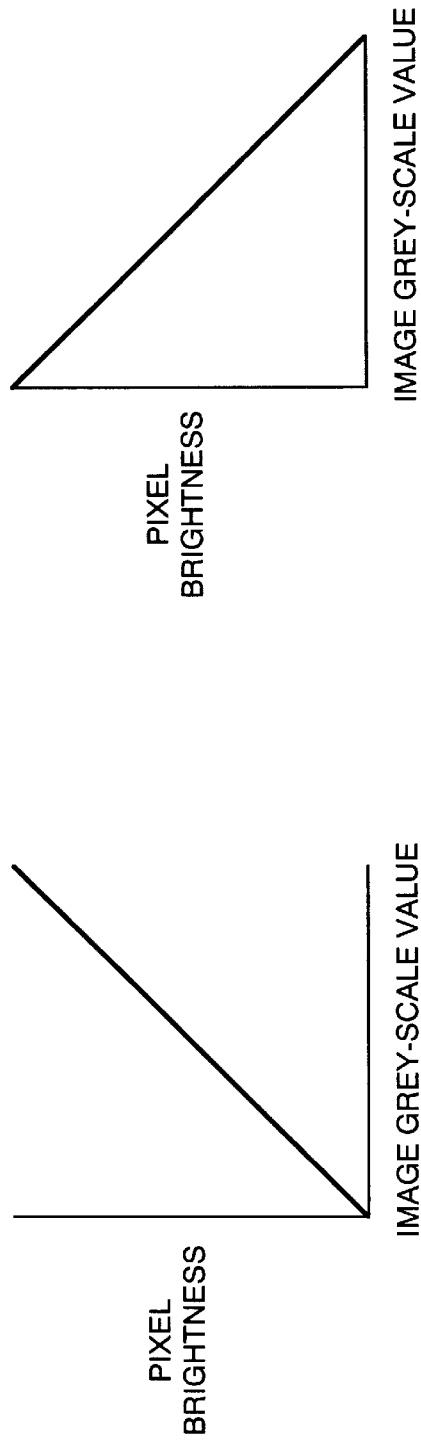

STEREO RADIOGRAPHY

This is a continuation of application Ser. No 08/079,363, filed Jun. 18, 1993, now abandoned, which is incorporated in its entirety herein by reference.

MICROFICHE APPENDIX

The disclosure in this case includes a microfiche computer program listing comprising . . . microfiche and . . . frames. The listing is being initially submitted in printed form.

BACKGROUND OF THE INVENTION

The present invention relates to x-ray systems and more particularly to apparatus for providing to a user a medically useful stereoscopic densitometric image of a three dimensional object such as a human breast.

While it has previously been proposed to implement stereoscopic visualization of x-ray images, such prior art systems have apparently not been medically successful for various reasons, largely failure to produce left and right images which can be successfully fused without visual strain by normal viewers such as medical doctors. As is understood by those skilled in the field of visual perception, the successful fusing of left and right images to obtain a natural and meaningful stereoscopic visualization is easily disrupted by any of a large number of possible imperfections or inconsistencies in the two images which are to be fused. For example, if the left and right images are generated on different cathode ray tubes (CRTs), as in the Sklebitz et al. disclosure of U.S. Pat. No. 4,769,701 it is extremely difficult to obtain to avoid differences in scale and in registration between the two tubes. Mis-registration, particularly in the vertical direction, is extremely disturbing to the ability of most viewers to effect subjective fusing of the images. Like Sklebitz et al., the system shown in the Simon Pat. No. 3,073,05 utilizes a pair of CRTs for display. Similarly, if different cameras or different regions of the same vidicon camera are utilized for the left and right images, e.g., as proposed in the Itoh U.S. Pat. No. 4,578,802, registration of the images may depend upon essentially perfect linearity of the vidicon scanning. Further, the spatial resolution of the vidicon tube is typically not adequate. In the Itoh system the right viewed and left viewed visual images are simultaneously displayed on a monitor with separation being effected by polarized glasses or a lenticular sheet system. Neither of these are described in detail but are believed to involve differentiating masks over the face of the monitor.

It has also been proposed to differentiate left and right images by utilizing different colors, e.g., as in the Euler et al. disclosure of U.S. Pat. No. 3,309,519. However, while the fusing of left and right images of different color can be accomplished, though with some difficulty, when viewing essentially solid objects, it becomes difficult in the extreme when the three dimensional images are densitometric, as in the case of x-ray images, so that the user's view in effect penetrates the object being viewed. This problem is particularly acute where the features being looked for, such as tumors and calcifications in the case of a human female breast, may exhibit only subtle densitometric differentiation from surrounding tissue.

There is also substantial prior art regarding the taking of stereotaxic images of an object such as a human breast but the purpose of obtaining such images is to facilitate the accurate placement of a localization needle within the object which is accomplished by the localization of visual landmarks in each of two images from points of view separated by a relatively wide angle and the images are not intended to be viewed simultaneously or fused by the user to yield a true three-dimensional view.

Among the several objects of the present invention may be noted the provision of a novel stereoscopic x-ray system which allows a user to readily fuse left and right viewed images so as to achieve stereopsis; the provision of such a system which provides highly accurate registration and matching of left and right viewed images; the provision of such apparatus which allows the stereoscopic visualization of features which are subtly differentiated in density; the provision of such a system which allows great flexibility in the presentation of stereoscopic x-ray images; the provision of such a system which provides highly accurate and medically useful visualization; and the provision of such a system which is highly reliable and which is of relatively simple and inexpensive construction. Other objects and features will be in part apparent and in part pointed out hereinafter.

SUMMARY OF THE INVENTION

The apparatus of the present invention provides to a user a stereoscopic densitometric image of a three dimensional object such as a human breast. The apparatus uses x-ray detecting means for converting x-ray images into electronic signals. The detecting means is exposed, through the object, with x-rays successively from two points separated by a preselected angle relative to the detecting means. The signals generated by the detecting means during the successive exposures are digitized and stored. A video display is driven to generate, on successive frames, alternating images based on respective ones of the stored signals and the eyes of a user viewing the display are alternately occluded in synchronism with the alternation of the images, thereby to provide stereoscopic view of the three dimensional object.

BRIEF DESCRIPTION OF THE DRAWINGS

FIGS. 9–12 illustrate transfer functions which can be applied to image data being displayed by the apparatus of FIG. 1 to adjust brightness and contrast.

Corresponding reference characters indicate corresponding parts throughout the several views of the drawings.

DESCRIPTION OF THE PREFERRED EMBODIMENT

Figure 1:
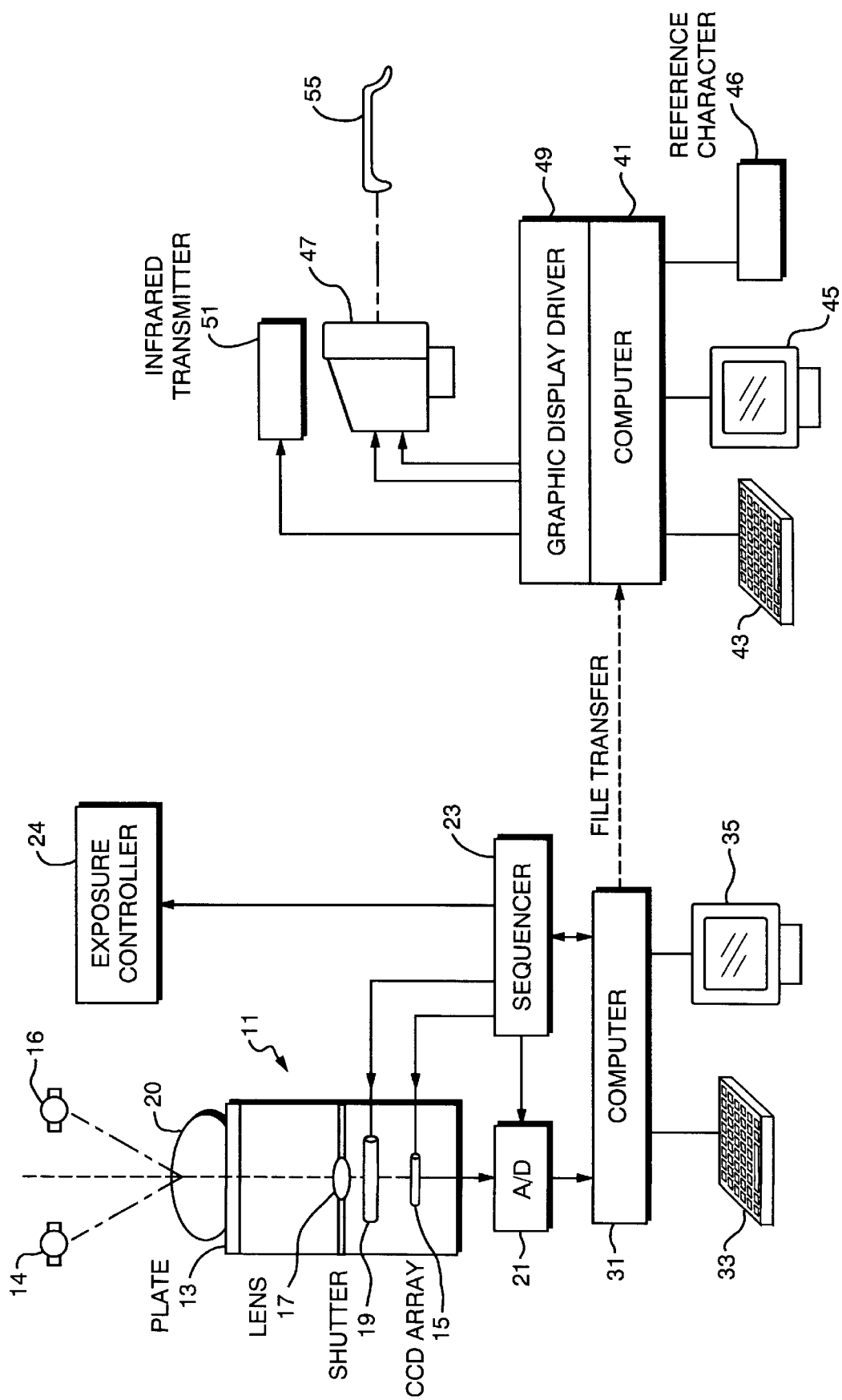
FIG. 1 is a diagrammatic illustration of a stereoscopic x-ray system constructed in accordance with the present invention.

While solid state detectors for the direct detection of x-ray images are being developed and could be used in the system of the present invention, the particular embodiment being described herein uses an electronic x-ray camera which employs a phosphor or fluoroscopic plate as designated by reference character 13. As is understood, the fluoroscopic plate 13 contains phosphors which, when struck by x-rays, give off light so as to produce a light image corresponding to the x-ray image. The light image provided by the plate 13 is coupled to a CCD (charge coupled device) array 15 by a lens 17, the light passing through an electrically operated shutter 19.

A three dimensional object which is to be examined, designated by reference character 20 is positioned above the fluorescent plate 13. In the case of a human breast, it may be compressed and held motionless by suitable clamping plates (not shown) as is conventional in the art. The fluorescent plate 13 is irradiated, through the object, by x-rays from two separate directions, designated by reference characters 14 and 16, which are separated by a preselected angle. An angle of about six degrees is appropriate in the case of a mammogram.

While two separate x-ray sources might be used for the successive images, a single source may be used by mounting it on an arm or stand which can be pivoted around an axis appropriately aligned with the object to be viewed.

As is understood by those skilled in the art, the CCD array 15 can be driven to provide an analog signal which, over time, represents the light amplitude incident on the array at successive points over the face of the array. This amplitude signal is converted to a corresponding sequence of digital values by an analog to digital (A to D) converter 21. In the embodiment being described, the A to D converter 21 provides fourteen bits of resolution, allowing for a wide dynamic range of nominal exposure values. A sequence controller 23 controls the opening of the shutter 19, the energization of the CCD array 19 and the operation of the A to D converter 21. The sequencer 23 also provides a synchronizing signal for triggering the energization of the x-ray source exposure controller 24 after the shutter has been opened and before the image is read out from the CCD array.

The sequence of digital values obtained from the A to D converter 21 are provided to a computer 31 where, after being buffered in memory, they are stored as a disk file which represents the corresponding x-ray image. As is conventional in data acquisition contexts, handshaking control signals provide cooperative interaction between the sequencer 23 and the computer 31. Preferably, a separate file is created for each image, e.g., left and right, and, in actual practice, images can be taken at several different angles and pairs can be arbitrarily selected for stereoscopic viewing as described in greater detail hereinafter. As is conventional, the computer 31 will typically be provided with a keyboard 33 and system monitor 35 by means of which the user can control the storage and file generating facilities provided by conventional computer operating systems.

While the same computer which acquires the image data could be utilized for controlling the generation of a stereoscopic display in accordance with the present invention, it will typically be appropriate that the display be operated under the control of a separate computer and that the image files be transferred, e.g., by data network communications or floppy disk, from one computer to the other. In FIG. 1, the second computer is designated by reference character 41 with its keyboard and system monitor being designated by reference character 43 and 45 respectively. Preferably, the display computer is provided with a so-called mouse type of pointing device as indicated by reference character 46. In addition to the usual system monitor 43, the computer 41 also controls a high refresh rate, high resolution graphics video display CRT 47 through graphic display driver circuitry designated generally by reference character 49.

Computer 41 both processes the stored data and the image file and controls display driving circuitry to generate the stereoscopic images for the user utilizing programs as described hereinafter. In the particular embodiment being described herein, the computer 41 is implemented by means of a so called IBM-compatible personal computer utilizing an Intel 486 processor running under the MS DOS 5.0 and Windows 3.1 operating system programs which are products of Microsoft Corporation of Belleview, Wash. The image data handling and display driver programs described in greater detail hereinafter are written in the Visual Basic programming language which is also a product of Microsoft Corporation and which is particularly adapted for use in the Windows operating system environment In the particular embodiment being illustrated, the display driver circuitry is implemented by means of a graphics system sold by Matrox Electronic Systems, Ltd. of Dorval, Quebec, Canada as a standard modification of its model IM-1280, the modification being to support stereo image display. This graphics system is configured as an add in card for IBM compatible personal computers and interfaces directly with the EISA (extended IBM PC-AT type) bus.

In the particular embodiment being described by way of illustration, the graphics display CRT 47 is operated in a mode in which each image is 1024 pixels wide ×512 lines or pixels high with a refresh rate of 120 non-interlaced frames per second. As is understood, the term non-interlaced means that a complete image is displayed in a single-frame and that successive frames are raster scanned over the same paths. In accordance with the practice of the present invention the two images to be viewed stereoscopically are supplied to the same CRT on alternating frames. Since the same CRT is utilized for both images such nonlinearities in scanning as do occur will be exactly the same for both images.

The user, i.e., a physician who wishes to view the images stereoscopically, wears a set of eye glasses 55 in which each lens is provided with a liquid crystal shutter. The shutters are operated in alternation so that only one eye is seeing at any given instant. The graphics driver 49 provides a synchronizing signal to an infrared transmitter 51 which triggers the alternating operation of the glasses so that the operation of the left and right shutters are synchronized with the presentation of the alternating images to the graphics monitor 47. In this way each eye views only a respective one of the images. Suitable glasses incorporating liquid crystal shutters together with a mating infrared transmitter for video synchronization are available from Stereographics Corporation of San Raphael, Calif., as is a suitable graphics CRT.

Figure 2:
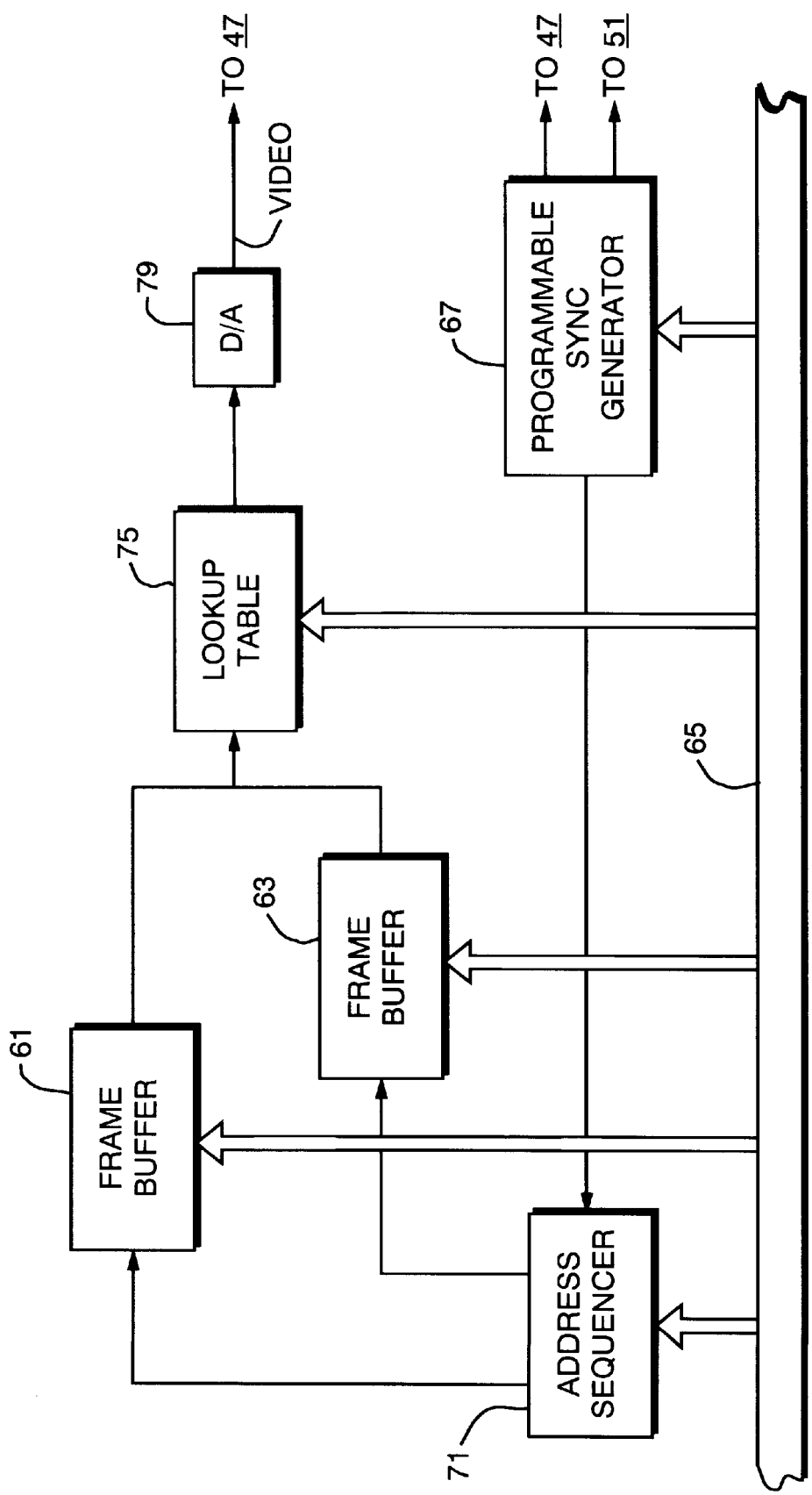
FIG. 2 is a block diagram of display driver circuitry employed in the system of FIG. 1.

The Matrox IM-1280 graphics display driver is a flexible system which can be user configured under software control to provide a wide variety of operating modes. FIG. 2 is a simplified diagram illustrating a configuration of the Matrox IM-1280 which can be used for stereoscopic image generation in accordance with the present invention as implemented by the software described hereinafter. A pair of frame buffers 61 and 63 are provided for storing the data representing the two images to be displayed in alternation. As is understood, the buffers 61 and 63 are implemented by sections of memory. Preferably, and as implemented by the IM 1280, the memory space available for each image is somewhat larger than needed, e.g., 1280×1024 locations so that the buffer actually controlling the display can be considered to be a shiftable window into the memory space. Boundaries of the window being displayed are controlled by software pointers.

The IM-1280 in fact incorporates sufficient memory for four such definable windows and the rapid switching between the windows can be used to generate stereoscopic viewing from changeable points of view as described hereinafter. Alternately, the memory can be configured to provide higher resolution or finer shading, i.e., 16 bits of grey scale for each frame.

For the purposes of the following general description each display buffer may be considered to be 1024×512×8 bits so that eight bits are available for defining the brightness at each point in the 1024×512 image space. In order to fully utilize the 8 bits of resolution available, the input data is transformed so that the range of amplitude values in the original 14 bit acquired image is mapped into the available 8 bits. In the particular embodiment being described, this mapping is performed by the software described hereinafter prior to loading the frame buffers. Essentially this transformation is performed by generating a histogram of the fourteen bit input data and then mapping the most common values into an eight bit range which is then loaded into the frame buffer, i.e., through the computer system bus as designated by reference character 65. A programmable synchronizing signal generator 67 provides appropriately timed synchronization signals to the graphics display CRT and to the infrared transmitter which controls the liquid crystal user glasses. The time base of the synchronizing signal generator is also used to drive an address controller 71 which sequences through the addresses of the frame buffers 61 and 63, as defined by the software pointers, for reading out the stored information during display. As indicated previously, the two buffers are in fact typically different regions of the same memory system and the two regions are read out in alternation by the address sequencer 71.

Rather than directly controlling the brightness of the display, the data values read out from each frame buffer are applied as indices into a lookup table, designated by reference character 75. The values loaded into the lookup table 75, in effect, establish a transfer function which can alter the effective brightness and contrast of the image being displayed. The values read out from the lookup table are applied to a digital to analog convertor 79 which generates the video signal driving the display.

Figure 3:
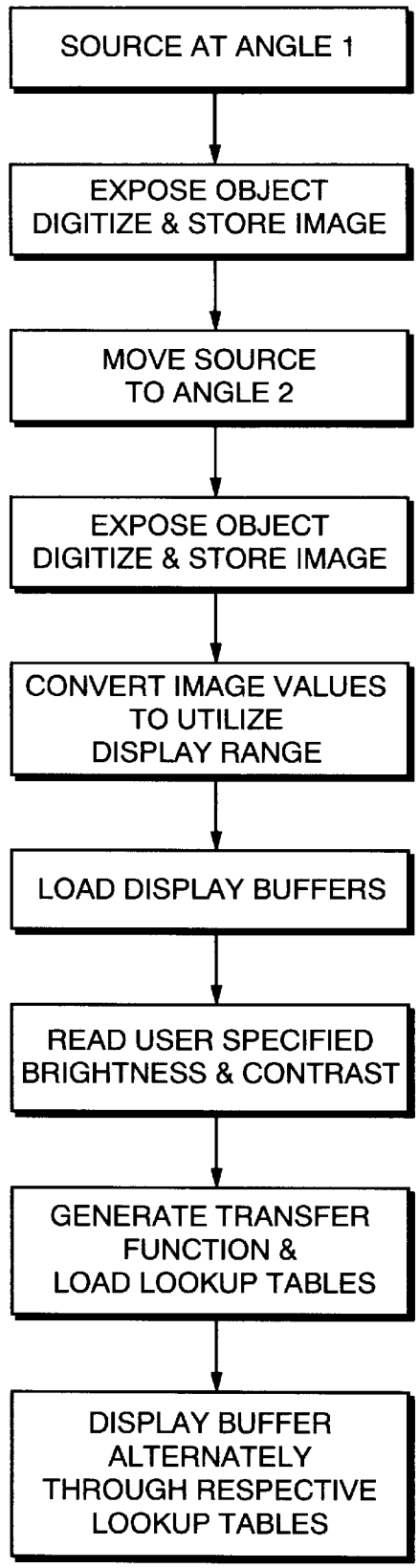
FIG. 3 is a flow chart illustrating operation of the system of FIG. 1.

FIG. 3 is a flow chart illustrating in somewhat simplified form the typical sequence of operations performed in acquiring stereographic images and displaying them in a manner which is medically useful.

As indicated previously, the program which sets up and runs the stereoscopic display is written in the Visual Basic programming language and the program which is listed in the Microfiche Appendix hereto utilizes various facilities of the Windows operating system to facilitate user control of brightness and contrast of the images being viewed. In particular, the user can employ a click and drag facility controlled by the mouse pointing device 46 to set various slide controls shown on a control screen for adjusting contrast, brightness and other parameters. The program in the listing also makes calls on software components provided by Matrox with the IM-1280.

Figure 4:
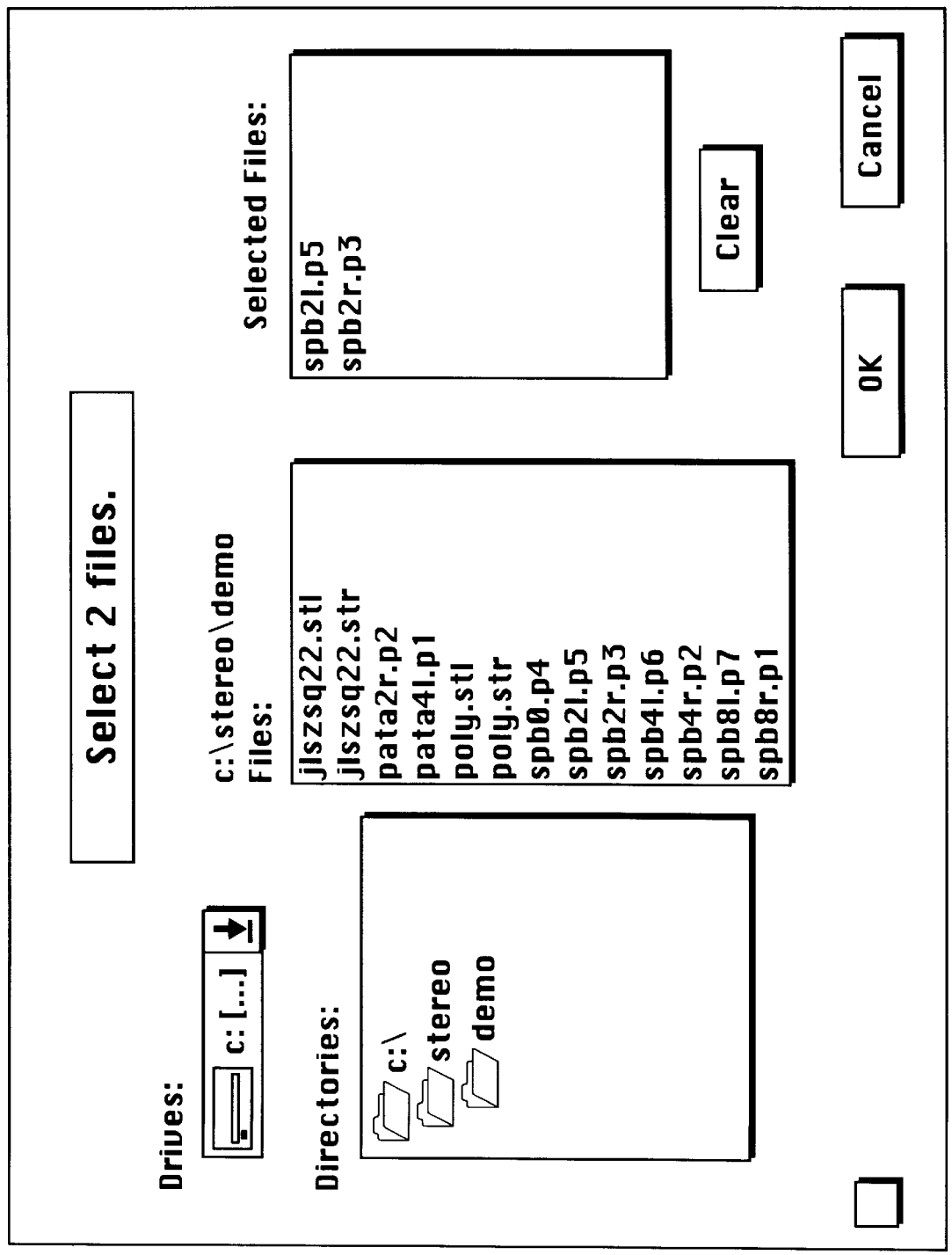
FIGS. 4–8 are illustrations representing control screens which can be utilized by the user to select images for viewing and to adjust and control the images being viewed for best differentiation of features within an object being examined.

Representative control windows are illustrated in FIGS. 4–8. FIG. 4 illustrates a file selection window which shows the user the active directory, lists the files available and allows him to select files for loading into the display buffers. As indicated previously, in the present implementation up to four files can be selected for such loading.

Figure 5:

FIG. 5 illustrates a control window which allows the user to select one of three display modes and which shows the files being displayed. This display mode includes a MONO mode which shows the same image to both eyes, a STEREO PAIR mode which displays a single stereo pair and a STEREO SERIES mode which displays a sequence of stereo pairs as a timed sequence as described hereinafter. As is conventional, a mode can be selected by positioning a cursor on the corresponding label and activating a button on the mouse 46.

Figure 6:
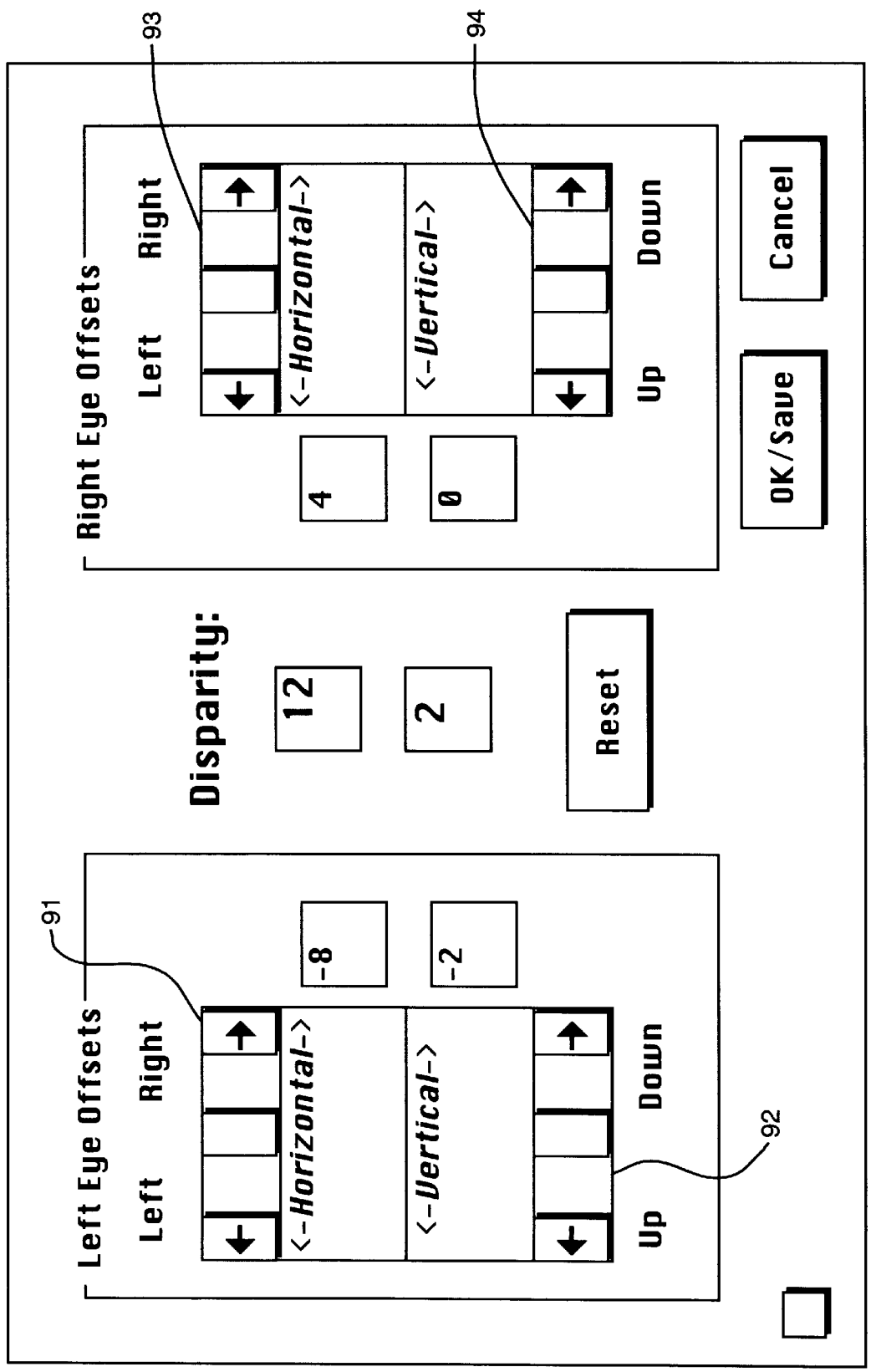

FIG. 6 is a control window which allows the user to manipulate the vertical and horizontal registration of the two images comprising a stereo pair. This allows the user to correct for any possible misalignment in the original image capture and to effectively change the image depth plane that is perceived by the viewer to lie at the surface of the display monitor. Changing the settings of the slider controls 91–94 obtains the desired offsets by changing the pointer values which define from where, within the available memory space, the image data window is read. The control window includes value displays which provide the user with information regarding the offset, both as an absolute value for each image and as relative disparities and offsets of the right eye relative to the left eye, stated in units of display pixels.

Figure 7:
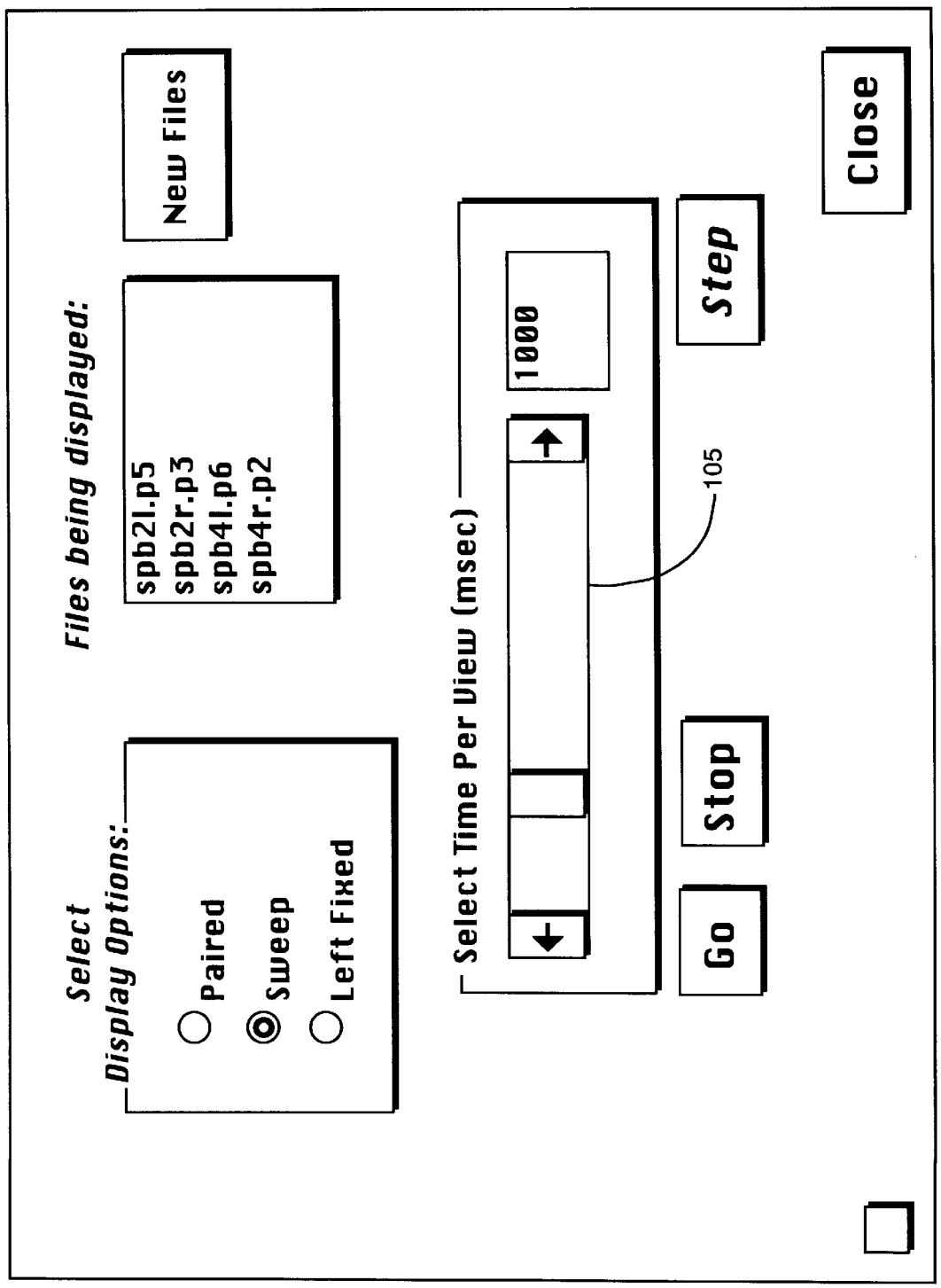

As indicated previously, the user can choose to view successions of image pairs in timed sequence and the control window of FIG. 7 allows the user to select among several display modes. In the PAIRED mode two stereo pairs are displayed alternately, each for a duration specified by the setting of the slider bar. In the SWEEP mode, the first two files are first shown to the left and right eyes respectively then the second and third files are shown to left and right eyes and then the third and fourth files are shown to the left and right eyes. The effect is essentially that of providing the user with a shifting point of view on the object being displayed. The series is then swept backwards to the original pairs where the cycle starts over. A changing point of view can, in some circumstances, enhance the 3-D perception, and aid in spotting densitometric anomalies. Again, the duration of each step in the cycle is controlled by the setting of the slider bar 105.

In the LEFT FIXED mode the first file is always presented to the left eye while the second, third and fourth files are shown in succession to the right eye. Again the right eye series is then swept backward to the original pair and the cycle begins again with timing being controlled by the slider bar. The perceived effect is of the 3-D object being rotated and enlarged cyclically. From the STOP state the various cycles can be single stepped with the step button shown in the control window.

Figure 8:
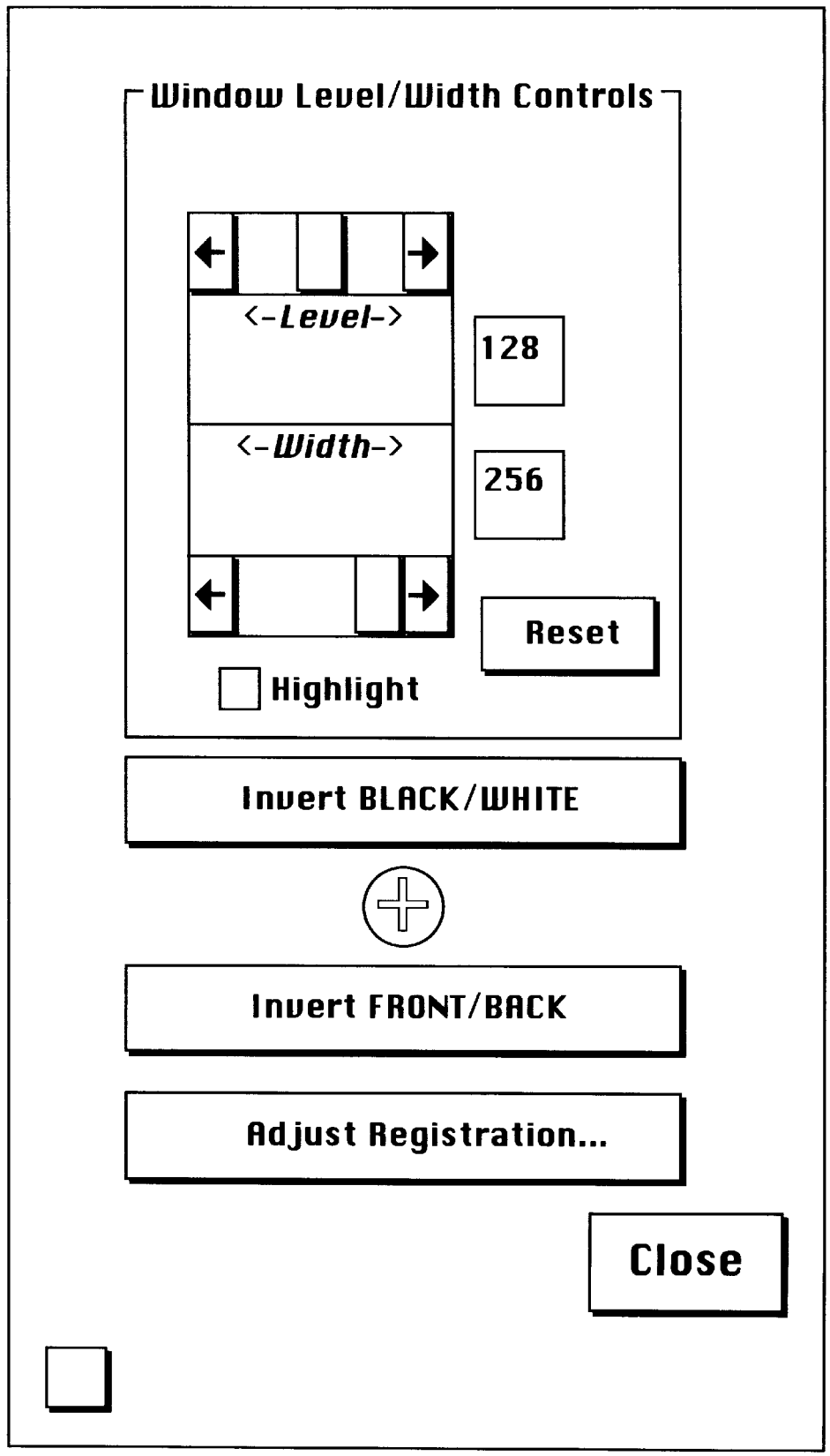

The control window illustrated in FIG. 8 allows the user to alter the gray scale appearance of the displayed images by changing WINDOW LEVEL and WINDOW WIDTH in the look up table to obtain different transfer functions as described. The user can also activate a HIGHLIGHT mode in which a specified window of gray scale values is brightened. The user can also invert the gray scale or invert displayed depth. Also the user can bring up the ADJUST REGISTRATION window of FIG. 6 by clicking on the appropriate button or control bar. As indicated previously, changes in gray scale appearance are effected by loading appropriate tables or values into the look up table 75 of FIG. 2 to obtain corresponding transfer functions. Various types of transfer functions that are useful are illustrated in FIGS. 9–12.

FIG. 9 illustrates a straightforward linear transfer function in which image gray scale values transform one-to-one to pixel brightness. The perceptual effect of this transfer function is that the image appears to be lit from the front, which highlights a structural detail.

FIG. 10 illustrates a transfer function in which gray scale values are essentially reversed in transferring to pixel brightness. The perceptual effect of this transfer function is that the image appears as if lit from behind. This highlights shapes in the image which are perceived as if in silhouette.

FIG. 11 illustrates a transfer function in which a window of gray scale values in the original image is expanded to fill the full range of pixel brightness available in the display. The relative steepness of the transfer function corresponds to increasing the contrast in the display. As is understood, such a transfer function can also be shifted right or left so that corresponding portions of the original gray scale are expanded. The range of gray scale values so expanded is designated as the "width" of the window in the control window of FIG. 8 while the lateral position is designated as "level". Portions of the gray scale outside of the window are effectively eliminated. This can be useful for effectively removing features not of interest which would otherwise increase the complexity of the image.

FIG. 12 illustrates a repetitive transfer function in which bands of the original gray scale values are expanded. This has the effect of increasing perceptible differences between subtle differences in original gray scale though it also introduces abrupt jumps in brightness. The effect, however, is medically useful in that it allows perception of features which might not otherwise be distinguishable.

Another feature provided by the control window of FIG. 8 is the front to back depth reversal of the stereo image. This is obtained by a software reversing of the left and right images. As will be understood by those skilled in the visual perception arts, this reversing of what is seen by the left and right eyes effectively reverses depth in the image, flipping the image from front to back. This can be useful in examining features which are deeper within the image, as compared to the nearer features which might otherwise obscure the users view by capturing his attention.

In view of the foregoing it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Apparatus for providing to a user a stereoscopic densitometric image of a three-dimensional object, said apparatus comprising:

means for detecting an x-ray image over a preselected region and for converting said image into electronic signals;

means for exposing said detecting means through said object, with x-rays successively from two points separated by a preselected angle relative to said region thereby to generate respective x-ray images;

means for digitizing and storing the respective electronic signals generated by said detecting means during successive exposures;

a video display providing successive image frames at a rate substantially higher than user perceivable flicker;

means for driving said display to generate, on successive frames, alternating images based on respective ones of said stored signals;

means for alternately occluding the eyes of a user viewing said display in synchronism with the alternation of said images thereby to provide to said user a stereoscopic view of said three-dimensional object; and means for progressively changing alternating buffers from which windowed regions are read out thereby to provide a shifting point of view.

2. Apparatus as set forth in claim 1 wherein said means for driving said display includes means for mapping the amplitude of each of said stored signals into a brightness level in the corresponding frame according to a preselectable transfer function.

3. Apparatus as set forth in claim 2 wherein said transfer function is provided by a table stored in digital memory.

4. Apparatus as set forth in claim 3 wherein said table is addressed by the stored digitized values of said signals.

5. Apparatus as set forth in claim 4 wherein the values stored in said table can be changed during display.

6. Apparatus as set forth in claim 4 wherein said table stores cyclically repeating values thereby to produce banded brightness values in said image.

7. Apparatus as set forth in claim 2 further comprising means for switching an image seen by a viewer's left eye to a viewer's right eye and for switching an image seen by said viewer's right eye to said viewer's left eye.

8. Apparatus as set forth in claim 2 wherein the transfer function essentially eliminates selected portions of the gray scale of the images presented to a viewer.

9. Apparatus as set forth in claim 2 wherein the transfer function accentuates gray scale difference over a preselectable range of stored values.

* * * * *

UNITED STATES PATENT AND TRADEMARK OFFICE
CERTIFICATE OF CORRECTION

PATENT NO : 6,031,565
DATED : February 29, 2000
INVENTOR(S) : David J. Getty, et al.

It is certified that error appears in the above-identified patent and that said Letters Patent are hereby corrected as shown below:

In Col. 1, prior to line 12, "BACKGROUND OF THE INVENTION", please enter the following:

-- STATEMENT REGARDING FEDERALLY SPONSORED RESEARCH OR DEVELOPMENT

This invention was made with Government support under Contract No.DAMD17-96-C-6079 awarded by U.S. Army Medical Research. The Government has certain rights in this invention. --

Signed and Sealed this

Twenty-second Day of May, 2001

Attest:

NICHOLAS P. GODICI

Attesting Officer

Acting Director of the United States Patent and Trademark Office